(12) United States Patent
Tenne

(10) Patent No.: US 8,690,935 B2
(45) Date of Patent: Apr. 8, 2014

(54) STENT DELIVERY SYSTEM WITH THREADED ENGAGEMENT AND METHOD

(75) Inventor: Dirk Tenne, Miami Beach, FL (US)

(73) Assignee: Depuy Synthes Products, LLC, Raynham, MA (US)

( * ) Notice: Subject to any disclaimer, the term of this patent is extended or adjusted under 35 U.S.C. 154(b) by 2013 days.

(21) Appl. No.: 11/380,831

(22) Filed: Apr. 28, 2006

(65) Prior Publication Data

US 2007/0255386 A1    Nov. 1, 2007

(51) Int. Cl.
*A61F 2/06* (2013.01)

(52) U.S. Cl.
USPC .......................... 623/1.11; 623/1.13; 623/1.23

(58) Field of Classification Search
USPC ........... 623/1.23, 1.11, 1.12, 1.13, 1.15, 2.11; 606/200
See application file for complete search history.

(56) References Cited

U.S. PATENT DOCUMENTS

| 5,288,711 | A | 2/1994 | Mitchell et al. | |
|---|---|---|---|---|
| 5,516,781 | A | 5/1996 | Morris et al. | |
| 5,563,146 | A | 10/1996 | Morris et al. | |
| 5,646,160 | A | 7/1997 | Morris et al. | |
| 5,807,327 | A * | 9/1998 | Green et al. | 623/1.11 |
| 6,673,106 | B2 | 1/2004 | Mitelberg et al. | |
| 6,818,013 | B2 | 11/2004 | Mitelberg et al. | |
| 6,833,003 | B2 * | 12/2004 | Jones et al. | 623/1.11 |
| 6,955,685 | B2 | 10/2005 | Escamilla et al. | |
| 6,960,227 | B2 | 11/2005 | Jones et al. | |
| 2002/0082683 | A1 | 6/2002 | Stinson et al. | |
| 2004/0236406 | A1 * | 11/2004 | Gregorich | 623/1.16 |
| 2005/0246010 | A1 * | 11/2005 | Alexander et al. | 623/1.12 |
| 2007/0123971 | A1 * | 5/2007 | Kennedy et al. | 623/1.11 |
| 2007/0293930 | A1 * | 12/2007 | Wang et al. | 623/1.11 |

\* cited by examiner

*Primary Examiner* — Corrine M McDermott
*Assistant Examiner* — Alexander Orkin
(74) *Attorney, Agent, or Firm* — Cook Alex Ltd.

(57) ABSTRACT

An expandable stent and delivery system are provided for treating body vessel defects, such as partially occluded blood vessels and aneurysms. The delivery system includes a core member having a threaded core member portion configured to interlock with a threaded strut member portion of the expandable stent. The expandable stent is mounted thusly onto the core member for movement within a delivery catheter and deployment to a body vessel defect. The deployment catheter is used to compress the interlocked threaded strut member portion into engagement with the threaded core member portion.

11 Claims, 3 Drawing Sheets

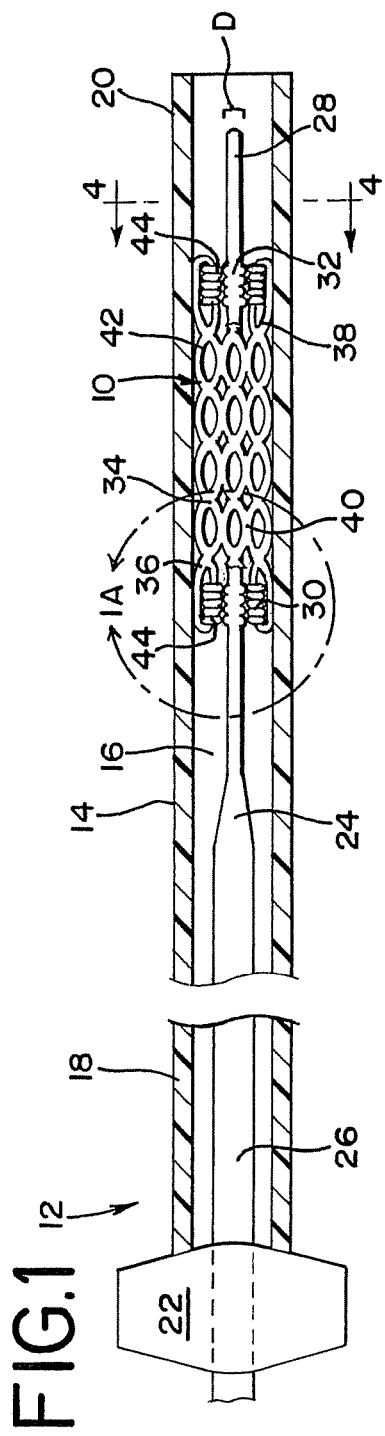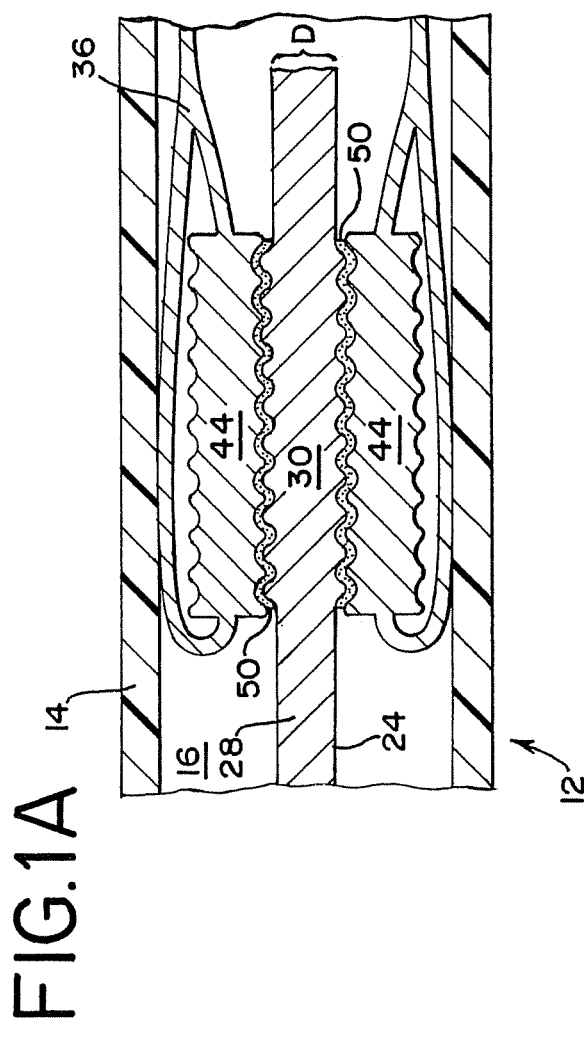
FIG.1
FIG.1A

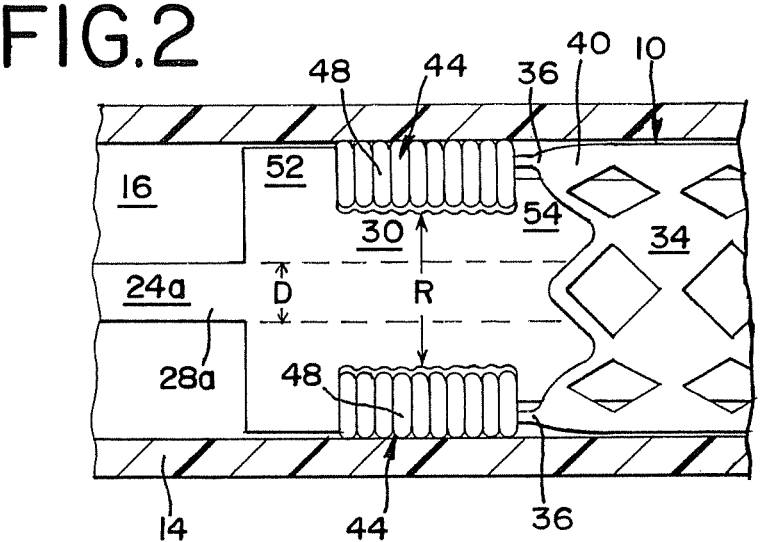
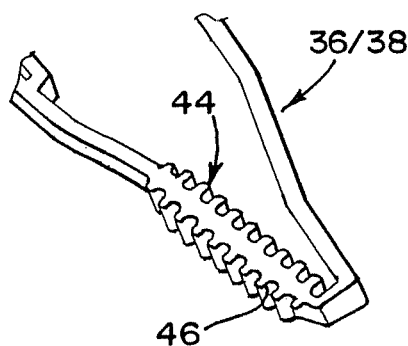
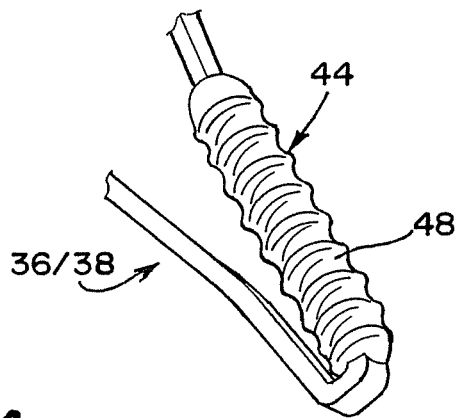
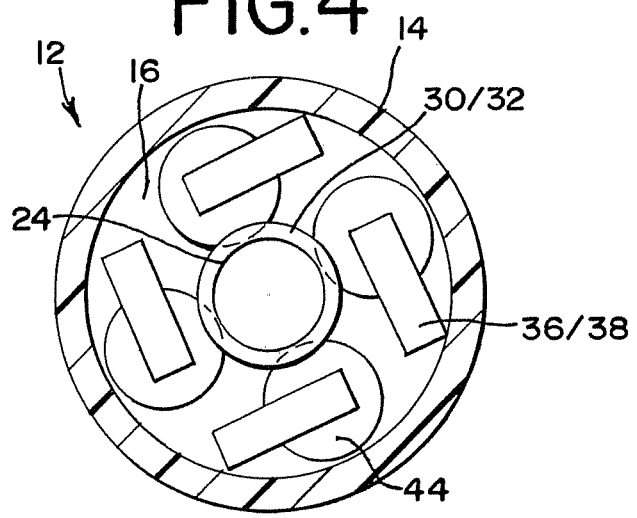

STENT DELIVERY SYSTEM WITH THREADED ENGAGEMENT AND METHOD

FIELD OF THE INVENTION

The disclosed invention relates to intraluminal therapeutic devices and delivery systems therefor, and more particularly, to expandable stents and delivery systems which may be used in the treatment of body vessel defects. This invention also relates to the deployment and repositioning of expandable stents within body vessels, especially those within the brain.

DESCRIPTION OF RELATED ART

On a worldwide basis, nearly one million balloon angioplasties are performed annually to treat vascular diseases such as blood vessels that are clogged or narrowed by a lesion or stenosis. The objective of this procedure is to increase the inner diameter of the partially occluded blood vessel lumen. In an effort to prevent restenosis without requiring surgery, short flexible cylinders or scaffolds, referred to as stents, are often placed into the body vessel at the site of the stenosis or defect. Stents are typically made of metal or polymers and are widely used for reinforcing diseased body vessels. Stents are also useful in treating aneurysms by providing an internal lumen to cover an aneurysm and thus reduce the flow of blood and the pressure within the aneurysm.

Some stents are expanded to their proper size using a balloon catheter. Such stents are referred to as "balloon expandable" stents. Other stents, referred to as "self-expanding" stents, are designed to elastically resist compression in a self-expanding manner. Balloon expandable stents and self-expanding stents are compressed into a small diameter cylindrical form and deployed within a body vessel using a catheter-based delivery system.

Stents have been developed with radiopaque markers to aid in the visualization of the stent upon deployment. Radiopaque markers facilitate the positioning of the stent within a body vessel by allowing a physician to determine the exact location, size, and orientation of the stent under x-ray or fluoroscopy. These markers are typically formed of a radiopaque material such as tantalum, zirconium, titanium, or platinum. Published U.S. Patent Application No. 2002/0082683 to Stinson et al., which is hereby incorporated herein by reference, discloses one such radiopaque marker comprised of a pigtail, knot, or ring, of tantalum wire wrapped around a crossing point of struts within a stent.

SUMMARY OF THE INVENTION

In accordance with one aspect of the present invention, an expandable stent and a stent delivery system are provided. The delivery system includes an elongated core member with a distal portion and a threaded core member portion disposed about the distal portion. The delivery system also includes a deployment catheter. The stent is a tubular member having a thin wall and a strut member extending away from the thin wall. The strut member defines a threaded strut member portion. At least a portion of the threaded strut member is threadably engageable with at least a portion of the threaded core member portion, and the two are interlocked when received in a lumen of the deployment catheter.

In accordance with another aspect of the present invention, a method of deploying an expandable stent within a body vessel is provided. The method involves providing an expandable stent and delivery system. The stent is mounted about a distal portion of an elongated core member of the delivery system. The stent has a strut member defining a threaded strut member portion and at least a portion of the threaded strut member portion is in threaded engagement with at least a portion of a threaded core member portion disposed at the distal portion of the elongated core member. The delivery system also includes a deployment catheter disposed about the stent to interlock the threaded strut member portion and the threaded core member portion. The expandable stent and at least a portion of the delivery system are inserted into a body vessel, and then the stent is positioned adjacent to a defect of the body vessel. When the stent is properly positioned, the deployment catheter is moved proximally with respect to the core member, which allows the stent to begin expanding within the body vessel. Finally, the deployment catheter is moved further proximally with respect to the core member, which allows the stent to fully deploy.

In accordance with yet another aspect of the present invention, a method of resheathing an expandable stent within a body vessel is provided. The method involves providing an expandable stent and delivery system. The stent is mounted about a distal portion of an elongated core member of the delivery system. The stent has a strut member defining a threaded strut member portion and at least a portion of the threaded strut member portion is in threaded engagement with at least a portion of a threaded core member portion disposed at the distal portion of the elongated core member. The delivery system also includes a deployment catheter disposed about the stent to interlock the threaded strut member portion and the threaded core member portion. The expandable stent and at least a portion of the delivery system are inserted into a body vessel, and then the stent is positioned adjacent to a defect of the body vessel. When the stent is properly positioned, the deployment catheter is moved proximally with respect to the core member, which allows the stent to begin expanding within the body vessel. If it is determined that the stent should be moved to a different position within the body vessel, then the deployment catheter is moved distally with respect to the core member, which forces the stent back into the cathether. When the stent is back in the cathether, the delivery system can be relocated.

Other aspects, objects and advantages of the present invention, including the various features used in various combinations, will be understood from the following description according to preferred embodiments of the present invention, taken in conjunction with the drawings in which certain specific features are shown.

BRIEF DESCRIPTION OF THE DRAWINGS

FIG. 1 is a partial sectional view of an expandable stent and a delivery system in accordance with an embodiment of the present invention;

FIG. 1A is an enlarged detail view of the expandable stent of FIG. 1 positioned within the delivery system;

FIG. 2 is an enlarged detail view of an alternative expandable stent positioned within an alternative delivery system;

FIG. 3A is an enlarged perspective view of a strut member having an integral threaded strut member portion, according to an aspect of the present invention;

FIG. 3B is an enlarged perspective view of a strut member having an outer layer according to another aspect of the present invention;

FIG. 4 is a cross sectional view of the stent and delivery system of FIG. 1, taken through the line 4-4 of FIG. 1;

DESCRIPTION OF THE PREFERRED EMBODIMENTS

Figure 5:
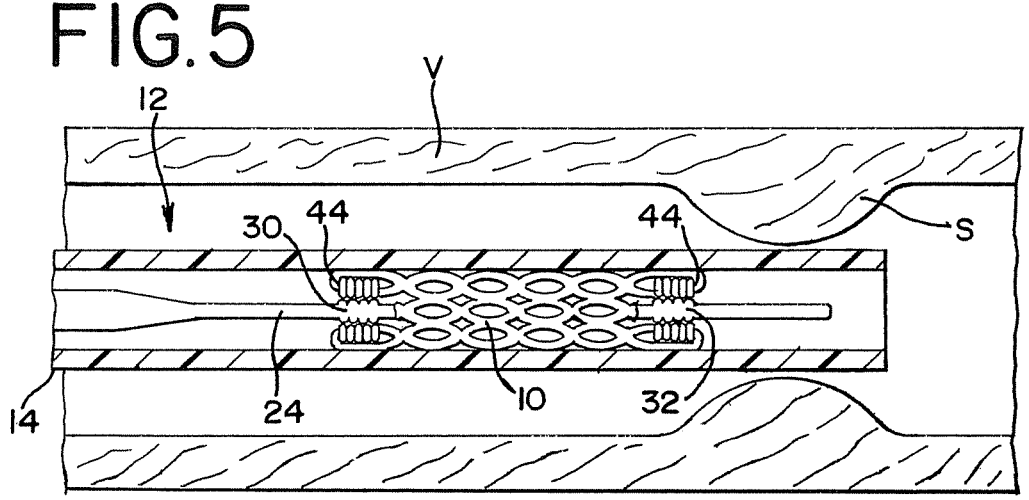
FIG. 5 is a partial sectional view of the expandable stent and delivery system of FIG. 1 in a body vessel.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIG. 1 illustrates an expandable stent 10 and delivery system 12. The delivery system 12 includes a deployment catheter or microcatheter 14 which takes the form of an elongated tube having a lumen 16. A proximal section 18 of the deployment catheter 14 is sufficiently flexible to traverse a body vessel, typically a blood vessel, but is sufficiently rigid so that it can be pushed distally through the body vessel. A distal section 20 of the deployment catheter 14 is preferably formed of a material that is more flexible than the proximal section 18, for enhanced maneuverability through a tortuous stretch of a body vessel. For example, the proximal section 18 may be substantially comprised of stainless steel, while the distal section 20 may be substantially comprised of a nitinol material in a superelastic state at body temperature.

A winged hub 22 may be coupled to the proximal section 18 of the deployment catheter 14. Preferably formed from a polymer material, the winged hub 22 is used to insert the deployment catheter 14 into a body vessel, such as a blood vessel within the brain of a patient.

The delivery system 12 also includes an elongated core member 24 which is formed of wire, preferably nitinol, but may also be formed from other metal alloys or a polymer material. The core member 24 is axially movable within the lumen 16 of the deployment catheter 14 and may be tapered so that a proximal portion 26 of the core member 24 has a greater diameter than an outer diameter D of a distal portion 28.

The distal portion 28 of the core member 24 includes at least one threaded core member portion 30, as illustrated in FIGS. 1 and 1A. The threaded core member portion 30 preferably defines a helical thread, similar to a screw thread, and may have a root diameter R greater than the outer diameter D of the core member distal portion 28, as illustrated in FIG. 2. In the embodiment of FIG. 1, the core member distal portion 2B includes a second threaded core member portion 32 spaced distally from the first threaded core member portion 30.

As for the expandable stent 10, it is removably mounted on the core member 24 for movement therewith through the deployment catheter 14. The expandable stent 10 may take on many different patterns or configurations, such as those disclosed in U.S. Pat. Nos. 6,673,106 and 6,818,013, both to Mitelberg et al. and both of which are hereby incorporated herein by reference. The stent 10 may be coated with an agent, such as heparin or rapamycin, to prevent stenosis or restenosis of the vessel. Examples of such coatings are disclosed in U.S. Pat. No. 5,288,711 to Mitchell et al.; U.S. Pat. No. 5,516,781 to Morris et al.; U.S. Pat. No. 5,563,146 to Morris et al.; and U.S. Pat. No. 5,646,160 to Morris et al., all of which are hereby incorporated herein by reference.

The illustrated stent 10 of FIG. 1 is laser cut from a tubular piece of nitinol to form a skeletal tubular member 34. The skeletal tubular member 34 has a thin wall, a small diameter, and when cut forms a plurality of cells which are created by a plurality of interconnected strut members. The nitinol is preferably treated so as to exhibit superelastic properties at body temperature.

The stent 10 includes at least one strut member 36, best illustrated in FIG. 1A, extending away from the tubular member 34. Preferably, the stent 10 includes a plurality of strut members 36 and 38 extending away from a proximal section 40 and a distal section 42, respectively, of the tubular member 34, as illustrated in FIG. 1. In one preferred embodiment, the stent 10 includes eight strut members, with four extending from each of the proximal and distal sections 40 and 42 of the stent tubular member 34. Each strut member 36 and 38 defines a threaded strut member portion 44, as described generally in U.S. Pat. No. 6,955,685 to Escamilla et al., which is hereby incorporated herein by reference.

A strut member 36,38 with an integral threaded strut member portion 44 is illustrated in FIG. 3A. As shown, the threaded strut member portion 44 is not a continuous helical thread, but has at least one row of teeth 46. However, the threaded strut member portion 44 preferably defines a helical thread to interact with the core member 24, as will be further described herein. Also, the threaded strut member portions 44 are preferably configured to generally occupy the space between the threaded core member portion 30,32 and the delivery catheter 14, as best illustrated in FIG. 4.

Depending on the material used to form the stent 10, there are a number of different ways to form the threaded strut member portion 44. For example, the threaded strut member portion 44 may be formed by cutting threads into the strut member 36,38 when the stent 10 is laser cut from a nitinol tubular member. Alternatively, a heat-molding technique may be used to form the threaded strut member portion 44 on the strut member 36,38. Those of ordinary skill in the art will appreciated that the present invention may be practiced regardless of the method of forming the threaded strut member portion 44.

Additionally, as illustrated in FIGS. 2 and 3B, an outer layer 48 may be deposited or wound about at least a portion of the threaded strut member portion 44 in order to increase its diameter or to provide other performance characteristics. For example, in a preferred embodiment, the threaded strut member portion 44 is wound with a radiopaque material defining a marker coil. The marker coil may be formed of a metallic or polymeric material that exhibits the characteristic of being radiopaque, such as tantalum or tantalum alloy. The marker coil may also be comprised of gold, gold alloy, platinum, platinum alloy, titanium, zirconium, bromine, iodine, barium, bismuth, or any combination thereof.

The outer layer is preferably applied onto the threaded strut member portion 44 so as to maintain the integrity of the underlying thread. Alternatively, the outer layer itself may define a thread, such as a row of teeth or a helical coil, in which case the strut member 36,38 need not be formed with a threaded strut member portion 44. This may be preferred, rather than forming the strut member itself with a thread. Accordingly, when used herein, the term "threaded strut member portion" refers to a configuration wherein a thread is provided by a threaded portion integrally formed in the strut member 36,38, by an integral threaded portion covered by an outer layer that preserves the underlying thread, or by an unthreaded strut member covered by an outer layer that is itself arranged to provide a thread.

In the case where an outer layer is applied to the strut member 36,38, the outer layer is preferably secured to the strut member 36,38 using an adhesive material, such as a UV adhesive which is thermally cured. In addition to increasing the diameter of the strut member 36,38, an outer layer provided as a marker coil serves as a radiopaque marker for improved visualization during the deployment of the stent within a body vessel.

As illustrated in FIGS. 1 and 5, the stent 10 is delivered to a body vessel V by the delivery catheter 14. The stent 10 and associated core member 24 are axially movable together within the delivery catheter 14. The stent 10 is removably locked onto the core member 24 by the interaction between the threaded strut member portion 44 and the threaded core member portion 30,32. Preferably, the threaded strut member portion 44 and the threaded core member portion 30,32 are provided as mating helical threads, such that at least a portion of the two may be interlocked by rotation, similar to a nut and bolt. In order to reinforce the interlocking relationship between the threaded strut member portion 44 and the threaded core member portion 30,32, an adhesive 50 may be applied therebetween, as illustrated in FIG. 1A. Furthermore, the strut member 36,38 may be configured to simultaneously contact the delivery catheter 14 and the threaded core member portion 30,32 in order to prevent the strut member 36,38 from radially expanding and detaching from the threaded core member portion 30,32. As described above, the proper fit between the threaded core member portion 30,32, the strut member 36,38, and the delivery catheter 14 may be achieved by adjusting the size of the strut member 36,38 or by increasing the diameter of the threaded core member portion 30,32, as illustrated in FIG. 2.

If only one threaded core member portion is provided, then it is preferably located proximally of the stent tubular member 34 to interlock with one or more threaded strut member portions 44 extending from the proximal section 40 of the stent 10. This is useful for retracting and repositioning the stent 10, as will be described herein. It may be preferred, however, to provide threaded core member portions 30,32 at each end of the stent tubular member 34 to discourage the stent distal section 42 from clinging to the delivery catheter 14 and "bunching up" during deployment of the stent 10.

By the above-described configuration, the stent 10 is locked onto the core member 24 for axial movement through the delivery catheter 14. In another embodiment, illustrated in FIG. 2, the interaction between the threaded strut member portion 44 and the threaded core member portion 30 is supplemented by provision of at least one cylindrical member associated with the distal portion 28a of the core member 24a and adjacent to the threaded core member portion 30. The general configuration and function of such cylinders may be seen in U.S. Pat. No. 6,833,003 to Jones et ale, which is hereby incorporated herein by reference.

In the illustrated embodiment of FIG. 2, the distal portion 28a of the core member 24a includes at least a first cylinder 52 and a second cylinder 54, which are separated by the proximal threaded core member portion 30. The cylindrical members 52 and 54 preferably have a greater diameter than the threaded core member portion 30, such that they define a gap in which the threaded core member portion 30 resides. It will be appreciated that the cylinders 52 and 54 further prevent the stent 10 from moving axially along the core member 24a while the threaded strut member portion 44 is interlocked with the threaded core member portion 30 and maintained within the gap.

In addition to constraining the axial movement of the strut member 36, the distal cylinder 54 is used to mount the expandable stent 10. As the stent 10 is positioned and mounted on the second cylindrical member 54, the strut members 36 extending away from the proximal section 40 of the tubular member 34 align with and are disposed within the gap, to interlock with the threaded core member portion 30. Similarly, if provided, the strut members 38 extending from the distal section 42 of the tubular member 34 align with and are disposed within a second gap, not illustrated, formed by a space between the second cylindrical member 54 and a third cylindrical member, not illustrated. In this configuration, the stent 10 is locked in place and may be pushed or pulled through the deployment catheter 14 without damaging or deforming the stent 10.

FIG. 5 illustrates the expandable stent 10 and delivery system 12 of FIG. 1 positioned within a body vessel V. Initially, the stent 10 is interlocked to the core member 24 by mating at least a portion of the threaded strut member portion 44 to at least a portion of the threaded core member portion 30,32. The core member 24 is then slid into the deployment catheter 14 to thereby hold the stent 10 in its constrained configuration. Alternatively, the core member 24 may be positioned within the delivery catheter 14, and then the stent 10 is compressed, fed into the catheter 14, and interlocked onto the core member 24. This may be preferred if the threaded core member portion 30,32 and the threaded strut member portion 44 are provided as mating helical threads. When the stent 10 is positioned within the delivery catheter 14, the delivery system 12 is inserted into the body vessel V and advanced distally until the stent 10 is aligned with a vessel defect S. Although the delivery system 12 is illustrated in use with a stenosed body vessel, it will be appreciated that it may be used with any other vessel defect treatable with a stent, such as an aneurysm.

Figure 6:
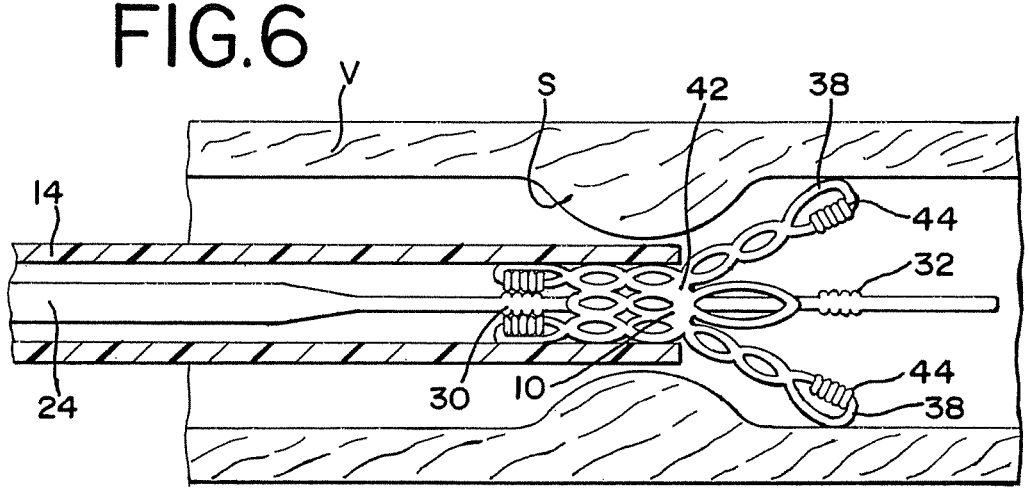
FIG. 6 is a partial sectional view of the delivery system with the deployment catheter moved proximally, allowing the distal section of the expandable stent to expand within the body vessel, while the proximal section of the expandable stent remains interlocked within the deployment catheter.

FIG. 6 shows the deployment catheter 14 moved proximally, releasing the distal strut members 38 and allowing the distal section 42 of the expandable stent 10 to begin expanding. During expansion, the distal section 42 of the stent 10 comes in contact with the wall of the body vessel V. If adhesive is provided between the threaded strut member portion 44 and the threaded core member portion 32, then it is preferably sufficiently weak so as to be overcome by the breakaway force of the expanding stent 10.

Figure 7:
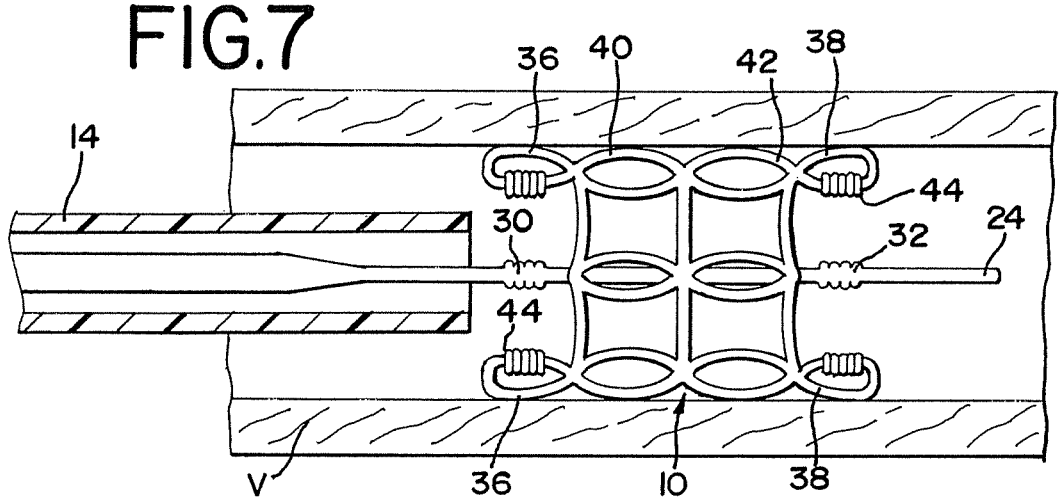
FIG. 7 is a partial sectional view of the delivery system with the deployment catheter moved proximally and the expandable stent fully expanded within the body vessel.

As illustrated in FIG. 7, the deployment catheter 14 is again moved proximally, releasing the proximal strut members 36 and allowing the stent 10 to fully expand. Once the stent 10 is fully deployed within the body vessel V, the core member 24 remains extended through the stent 10 and thus acts as a guide wire, providing a physician with easier access to locations within the body vessel distal of the stent 10.

If, during the deployment process, it is determined that the stent 10 should be relocated or realigned, the deployment catheter 14 may be used to resheath the stent 10. With the stent 10 positioned on the core member 24 as described above with reference to FIG. 6, the proximal threaded strut member portion 44 will remain interlocked on the proximal threaded core member portion 30. In this configuration, the stent 10 may be resheathed. To resheath the stent 10, the deployment catheter 14 is moved distally, thereby forcing the stent 10 back into the catheter 14 and onto the core member 24, compressing the distal section 42 of the stent 10, and forcing the distal strut members 38 into engagement with the distal threaded core member portion 32. The stent 10 and delivery system 12 may then be withdrawn or repositioned to a different location within the body vessel V.

When the expandable stent 10 has been properly positioned and fully expanded within the blood vessel V, as illustrated in FIG. 7, the delivery catheter 14 and the core member 24 are removed from the body.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. An expandable stent and stent delivery system comprising:
   a delivery system including an elongated core member having a longitudinal core member axis and a distal portion along the longitudinal core member axis, the distal portion of said elongated core member has integrally formed thereat a first threaded core member portion, and the first threaded core member portion has a plurality of threads having respective ridges projecting radially outwardly;
   an expandable stent having a compressed state and an expanded state that is a self-expanded state, said stent comprising a tubular member having a thin wall and a longitudinal stent axis substantially coaxial with the core member axis, the stent having a body portion including a proximal section and a distal section, a first strut member extending away from said thin wall in a direction generally parallel to the stent axis and offset radially outwardly from the stent axis, wherein said first strut member defines a first threaded strut member portion that does not lie along the body portion of the stent and that extends longitudinally away from and beyond either the proximal section or the distal section of the stent body portion, the first threaded strut member portion has a row of teeth, and wherein said ridges of the first threaded core member portion are threadably engageable with the teeth of said first threaded strut member portion;
   said distal portion of the elongated core member has a diameter such that the distal portion is radially spaced away from the stent body portion when the stent is in its compressed state; and
   a deployment catheter having a lumen extending therethrough and adapted for coaxial placement about said elongated core member such that said deployment catheter compresses the expandable stent from its self-expanded state to its compressed state and causes said first threaded strut member portion but not the body portion of the stent to be interlocked onto said first threaded core member portion by mating engagement between said first threaded core member ridges and said first threaded strut member portion teeth, while the core member distal portion remains spaced away from and does not interlock with the stent body portion.

2. The expandable stent and stent delivery system of claim 1, wherein a root diameter of said first threaded core member portion is larger than an outer diameter of said distal portion of said elongated core member.

3. The expandable stent and stent delivery system of claim 1, wherein said first strut member extends away from the proximal section of the expandable stent.

4. The expandable stent and stent delivery system of claim 3, further comprising a second strut member extending away from said proximal section of the expandable stent, wherein said second strut member defines a second threaded strut member portion that does not lie along the body portion of the stent and that extends longitudinally away from and beyond the proximal section of the stent body portion, and wherein said first threaded core member portion is threadably engageable with said second threaded strut member portion.

5. The expandable stent and stent delivery system of claim 1, further comprising a marker coil of radiopaque material applied to said first strut member and adapted to threadably engage at least a portion of said first threaded core member portion.

6. The expandable stent and stent delivery system of claim 1, further comprising a second threaded core member portion disposed about the distal portion of said elongated core member and a further strut member extending away from the expandable stent in a direction generally parallel to the stent axis and offset radially outwardly from the stent axis, wherein said further strut member defines a further threaded strut member portion that does not lie along the body portion of the stent and that extends longitudinally away from and beyond the distal section of the strut body portion, and wherein said second threaded core member portion is threadably engageable with said further threaded strut member portion as well as said first threaded strut member portion.

7. The expandable stent and stent delivery system of claim 1, further comprising a first cylindrical member disposed generally adjacent to said first threaded core member portion.

8. The expandable stent and stent delivery system of claim 7, wherein said deployment catheter compresses at least a portion of the expandable stent about said first cylindrical member.

9. The expandable stent and stent delivery system of claim 7, further comprising a second cylindrical member disposed about the distal portion of said elongated core member, wherein said first cylindrical member is spaced from said second cylindrical member to define a gap, and wherein said gap receives said first threaded core member portion.

10. The expandable stent and stent delivery system of claim 1, further comprising an adhesive between said at least a portion of said first threaded strut member portion and said at least a portion of said first threaded core member portion.

11. The expandable stent and stent delivery system of claim 10, wherein said adhesive is adapted to break when said first threaded strut member portion is moved out of said deployment catheter.

* * * * *